(12) United States Patent
Roesicke et al.

(10) Patent No.: US 9,662,070 B2
(45) Date of Patent: May 30, 2017

(54) CONTROLLABLE SENSOR INSERTION NEEDLE

(75) Inventors: Bernd Roesicke, Mannheim (DE); Andrea Rittinghaus, Neckarsteinach (DE); Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1203 days.

(21) Appl. No.: 13/294,643

(22) Filed: Nov. 11, 2011

(65) Prior Publication Data
US 2012/0078072 A1    Mar. 29, 2012

Related U.S. Application Data

(63) Continuation of application No. PCT/EP2010/056421, filed on May 11, 2010.

(30) Foreign Application Priority Data

May 13, 2009    (EP) .................................... 09160090

(51) Int. Cl.
*A61B 5/05*        (2006.01)
*A61B 5/00*        (2006.01)
(Continued)

(52) U.S. Cl.
CPC ........ *A61B 5/6846* (2013.01); *A61B 5/14532* (2013.01); *A61B 5/14546* (2013.01); *A61B 5/6848* (2013.01); *A61B 17/3468* (2013.01); *A61B 5/14865* (2013.01); *A61B 2017/00022* (2013.01); *A61B 2017/00477* (2013.01);
(Continued)

(58) Field of Classification Search
CPC . A61B 5/6846; A61B 5/6848; A61B 5/14507; A61B 5/14546; A61B 5/14865
See application file for complete search history.

(56) References Cited

U.S. PATENT DOCUMENTS 5,390,671 A    2/1995 Lord et al.
6,229,683 B1 *  5/2001 Goodwin-Johansson .... 361/233
(Continued)

FOREIGN PATENT DOCUMENTS

DE              101 17 286 A1    10/2002
DE    10 2004 002 472 A1     8/2005
(Continued)

*Primary Examiner* — Christian Jang
(74) *Attorney, Agent, or Firm* — Bose McKinney & Evans LLP

(57) ABSTRACT

An insertion device is proposed for at least partly inserting a subcutaneous device, more particularly a subcutaneous sensor for detecting at least one analyte, into body tissue. The insertion device has at least one insertion aid and at least one subcutaneous device. The insertion aid has at least one substantially rigidly designed base body, more particularly an insertion needle, for insertion into the body tissue. The insertion device is designed to generate an adjustable holding force between the base body and the subcutaneous device. The insertion device is designed to set the holding force during the insertion such that the subcutaneous device is held against the base body. The insertion device is furthermore designed to set the holding force after the insertion such that the subcutaneous device is detachable from the base body.

32 Claims, 6 Drawing Sheets

(51) Int. Cl.
  *A61B 5/145*  (2006.01)
  *A61B 17/34*  (2006.01)
  *A61B 5/1486*  (2006.01)
  *A61B 17/00*  (2006.01)
  *A61M 5/158*  (2006.01)

(52) U.S. Cl.
  CPC ........ *A61B 2560/063* (2013.01); *A61M 5/158* (2013.01); *A61M 2005/1585* (2013.01)

(56) References Cited

U.S. PATENT DOCUMENTS

| | | | |
|---|---|---|---|
| 6,498,870 B1 * | 12/2002 | Wu et al. ........................ | 385/18 |
| 2002/0023852 A1 * | 2/2002 | Mcivor .............. | A61B 5/14532 |
| | | | 206/305 |
| 2002/0032374 A1 * | 3/2002 | Holker et al. ................ | 600/373 |
| 2005/0230767 A1 * | 10/2005 | Park et al. .................... | 257/414 |
| 2007/0016149 A1 | 1/2007 | Hunn et al. | |
| 2007/0156126 A1 | 7/2007 | Flaherty | |
| 2008/0033399 A1 | 2/2008 | Hunn et al. | |

FOREIGN PATENT DOCUMENTS

| | | |
|---|---|---|
| EP | 0 678 308 A1 | 10/1995 |
| WO | WO 03/080169 A1 | 10/2003 |

\* cited by examiner

CONTROLLABLE SENSOR INSERTION NEEDLE

RELATED APPLICATIONS

This application is a continuation of PCT/EP2010/056421, filed May 11, 2010, which claims priority to EP 09 160 090.8, filed May 13, 2009, both of which are hereby incorporated by reference in their entirety.

BACKGROUND

The invention relates to an insertion device for inserting a subcutaneous device into body tissue, and to an insertion aid and a subcutaneous device for use in such an insertion device. Such insertion devices, subcutaneous devices and insertion aids are used in the field of medical diagnostics in particular, more particularly in the field of so-called home monitoring, more particularly for monitoring a concentration of at least one analyte in a bodily fluid, e.g. blood or interstitial fluid. However, other applications are also possible.

The field of medical diagnostics or therapy has disclosed subcutaneous devices, i.e. devices that are designed to be inserted, wholly or partly, into body tissue, e.g. interstitial fatty tissue. This introduction is also referred to as insertion or implantation. Examples of such subcutaneous devices can in particular be found in the field of diagnostics, more particularly in the field of long-term monitoring of subjects, for example within the scope of so-called "home monitoring" or else in a clinical context. Accordingly, the subcutaneous device can for example comprise at least one subcutaneous sensor, for example an electrochemical and/or optical sensor, for detecting at least one analyte in the body tissue and/or in a bodily fluid. Alternatively, or in addition thereto, the subcutaneous device may also comprise other types of medical devices, such as e.g. medication devices that can introduce specific active ingredients into the body tissue in a targeted and preferably dosed fashion. Without restricting further possible fields of application, embodiments incorporating the invention will substantially be described in the following text with reference to subcutaneous sensors.

Medical therapy or diagnostics often require that one or more physical and/or chemical parameters be detected in body tissue of a subject. Examples of such physical and/or chemical parameters are analyte concentrations of one or more analytes such as e.g. glucose. By way of example, a medical treatment, for example an administration of certain medicaments or a different embodiment of influencing the body or body functions of the subject, can be selected, depending on the detected parameters.

The prior art has disclosed a number of examples for, in particular, qualitative or quantitative detection of one or more analytes by implantable, subcutaneous sensors. Thus, the subcutaneous sensors may for example be based on electrochemical measurement principles and comprise one or more chemical substances (also referred to as "test chemicals" in the text below), which change one or more physically and/or chemically measurable properties if the at least one analyte to be detected is present. Examples of such test chemicals are test chemicals based on enzymes, which are used in e.g. electrochemical sensors. Other measurement principles are for example based on optical properties, in which at least one test chemical changes at least one optically detectable property if the at least one analyte to be detected is present. Reference can be made to all measurement principles within the scope of the present invention.

A technical and medical challenge consists of implanting (inserting) the subcutaneous device into the body tissue. Carrying out this insertion should cause as little pain as possible and it should be possible to place the subcutaneous device such that the latter can also remain, at least in part, in the body tissue for a relatively long period of time of e.g. a few hours up to a few days, and can for example supply measurement data. Therefore, the prior art has disclosed a number of insertion devices that, in addition to the subcutaneous device to be implanted, comprise one or more insertion aids. By way of example, such insertion aids may be wholly or partly embodied as insertion needles, for example in the form of cannulae, into which the subcutaneous device can be introduced or onto which the subcutaneous device can be applied in order to be implanted into the body tissue therewith. The insertion aid can subsequently be removed again, with the subcutaneous device at least partly remaining in the body tissue. In the process, part of the subcutaneous device may project out of the body tissue, for example for a later removal of the subcutaneous device.

The prior art often teaches introducing an elongate, subcutaneous sensor partly under the skin, for example with an insertion depth of between 10 and 20 mm, using a minimally invasive technique by means of a hollow needle. By way of example, this may be brought about perpendicularly or at an angle, for example at 45°. The skin of the subject is penetrated in the process. The hollow needle can once again be removed after the insertion and the sensor may remain in the skin or the tissue and be connected to an evaluation instrument, which e.g. is worn externally. Compared to their longitudinal extent, sensors are generally narrow in their width and thickness and are weak as a result thereof. Skin and tissue prevent the sensor from penetrating into the body tissue. In order to stabilize the sensor during the insertion, the latter should therefore be stabilized at times for the procedure as per the prior art. In the described prior art, this is generally brought about by the insertion aid as a separate auxiliary means, wherein the insertion aid for example is produced from steel, more particularly in the shape of a needle. The sensor must be held so that the sensor remains in the skin, even when the insertion needle is withdrawn. Since the sensor generally has a thickened holding and/or sensor contact region, which must likewise be removed from the insertion needle, the insertion needle generally has a slit design. The hollow needle formed thus may for example have a U-profile or an almost closed O-profile, or else an angular profile.

The insertion needle has in many cases been provided with a cutting edge at the front end for painless penetration of the skin and the body tissue. The needle shape of the insertion needle ensures that the force exerted by the body tissue onto the sensor front does not bring the sensor out of its stretched shape during the insertion of the sensor. The needle slit of the insertion needle to this end preferably has a narrower design than the sensor width; however, this requires a tapering in the sensor shaft region during the withdrawal and separation of the insertion needle from the sensor. It is alternatively possible for the needle slit to be arranged laterally (with respect to the flat sensor structure) on the insertion needle, with the width of the sensor significantly exceeding the sensor thickness. Here, the holding and contact region may protrude from the needle slit.

A technical challenge lies in releasing the sensor when the insertion needle is withdrawn. This can also be brought about by means of so-called "peel needles". Such peel needles may for example comprise a metal film rolled up to form a solid tube, which opens when the sensor projecting from the alignment is withdrawn and is resealed thereafter.

In principle, as an alternative to using an insertion needle, it is also possible to introduce a relatively flexible sensor under the skin without such an insertion aid. An option for such an insertion consists of using high insertion speeds. However, such applications are in principle disadvantageous because the insertion is as a rule afflicted with high uncertainty and because there is for example the risk of damaging the sensor during the insertion. Moreover, a mechanically complex apparatus is generally required.

Alternatively, or in addition thereto, use can also be made of sensor elements that have a locally increased rigidity. Thus, U.S. Publication No. 2006/0015024 A1 for example describes a transcutaneous medical element which has a distal section with a more flexible design than a more rigid proximal section that penetrates the skin surface. However, a disadvantage of such sensor elements is that the more rigid, proximal section also remains in the body tissue after the insertion, which may cause injury in the body tissue and increased infliction of pain.

The prior art generally describes different types of insertion devices and insertion aids in detail. Thus, European Patent No. EP 0 678 308 B1 for example discloses an insertion principle, in which a flexible feeler can be implanted into body tissue by means of a hollow insertion needle and an attachment foot. The insertion needle has a slit running along one side so that the insertion needle can be withdrawn from the feeler.

German Patent No. DE 103 06 013 A1 and U.S. Publication No. 2006/0030824 have disclosed a temperature-sensitive cannula for introduction into body tissue. The cannula is flexible in an introduced state, and has a rigid state below a critical temperature range and a flexible state above the critical temperature range. Prior to the introduction of the cannula into the body tissue, the former is cooled to a temperature below the critical temperature range by cooling and is thereby made more rigid. Hence the cannula is stiffened before the penetration, while the material may soften after the penetration.

German Publication No. DE 10 2004 002 472 B4 and U.S. Publication No. 2007/0016149 have disclosed a puncturing needle for introducing a product into the human or animal body. The puncturing needle has a distal needle section and a proximal needle section with different materials, wherein the distal needle section is more flexible than the proximal needle section.

German Patent No. DE 101 17 286 A1, U.S. Publication No. 2004/0158230 and U.S. Publication No. 2008/0033399 have disclosed a soft cannula, which has increasing resilience during the application. Prior to the application, the cannula has at least one material with adjustable hardness or at least two materials with different hardnesses, with the material of greater hardness being released during the application. Thus, the material changes its hardness properties during the application, which can mainly be traced back to the composition of the cannula.

PCT Publication No. WO 03/080169 A1 has disclosed an insertion needle, which has a needle body and a distal end section, for inserting a subcutaneous device. The distal end section has a tip. Furthermore, the needle body has a longitudinal depression that is designed for at least in part holding a subcutaneous device. By way of example, the subcutaneous device can be held on the needle body by means of one or more rigidly designed grippers such that although said subcutaneous device is held during the insertion, it can be pushed off the insertion needle when the insertion needle is pulled out of the body tissue.

The known insertion devices and insertion aids in principle have a few technical disadvantages, which must be accepted or must be overcome in a complex fashion. Thus, the generally flexible sensor shaft must, by means of the needle shape of the insertion needle, be prevented from deviating laterally during e.g. the insertion using an insertion needle. In general, in order to remove the insertion needle, the sensor must, in the process, deviate from the alignment between a front, distal part (sensor tip) and a rear, proximal part (contact piece and/or holder) or the insertion aid must be brought out of this line by means of its movement. By way of example, this problem is explained in detail in European Patent No. EP 0 678 308 B1. Both require a significant amount of mechanical complexity, such as e.g. the complicated design of the sensor, insertion needle and/or insertion needle and sensor guide at a defined angle or along a circular path. The dynamic insertion method illustrated above is also generally connected to significant mechanical complexity.

A further disadvantage of known insertion devices and insertion aids consists of the fact that hollow needles generally have a significantly larger cross section than simple needles. Accordingly, the skin is penetrated by a significantly larger cross section than the actual sensor profile, which can lead to increased levels of pain being felt and to increased tissue destruction.

A further disadvantage of known insertion devices and insertion aids lies in the reliability of the insertion, namely, that it is not always possible to ensure that the sensor does not slip relative to the insertion needle during the insertion of the insertion needle into the body tissue. On the other hand, it is not always reliably possible to ensure that the sensor remains in the body tissue and is not removed again from the body tissue together with the insertion needle when the insertion needle is removed from the body tissue.

SUMMARY

Embodiments incorporating the present invention provide an insertion device, an insertion aid and a subcutaneous device that addresses and largely avoids the disadvantages of known corresponding devices. More particularly, the insertion device disclosed herein allows a safe, reliable and pain-free insertion of the subcutaneous device into body tissue.

An insertion device for at least partial insertion of a subcutaneous device into body tissue is proposed. Here, within the scope of the present invention, an insertion is understood to mean an introduction, for example an implantation, of the subcutaneous device into the body tissue. Here, the terms "implant", "insert", "introduce", "set" and "embed" are used largely synonymously in the following text and imply at least partial passing of the subcutaneous device into the body tissue. The subcutaneous device may be introduced wholly or partly into the body tissue, wherein part of the subcutaneous device may optionally protrude from the body tissue, for example in order to be connected to a measuring device and/or an actuation and/or evaluation instrument. A subcutaneous device should generally be understood to mean a device that is implantable into body tissue. Here the term "subcutaneous" is used synonymously with the term "transcutaneous," which is likewise used extensively in the literature, because in both cases there may be an insertion into the body tissue, particularly through skin of a subject. However, in principle, another type of insertion, without penetrating the skin, is also possible, for example into already exposed body tissue (for example during surgery) and/or through body tissue not covered by skin within the proper meaning of the word and/or within the meaning of an epidermis. However, in general, the term "skin" can be interpreted quite broadly and may comprise e.g. an epidermis, a dermis, subcutaneous tissue or another type of skin. Here, the insertion may be completely through the skin or the skin itself may already in part be understood as body tissue, and so there may for example merely be an insertion through one or more of the uppermost skin layers.

The subcutaneous device may in particular have at least one medical function, more particularly at least one diagnostic and/or at least one therapeutic function. Accordingly, the subcutaneous device may for example be embodied as a subcutaneous sensor or comprise at least one such subcutaneous sensor, wherein the subcutaneous sensor is embodied to detect at least one analyte qualitatively or quantitatively. By way of example, the sensor may be embodied for qualitative and/or quantitative detection of at least one analyte in the body tissue itself and/or in one or more bodily fluids, such as blood and/or interstitial fluid, contained in the body tissue. The analyte may in particular be at least one metabolite. As an alternative to detecting at least one analyte, or in addition thereto, the sensor may in principle also be designed to detect at least one physical and/or chemical property of the body tissue and/or subject, such as e.g. a temperature, a blood pressure or the like. In the following text, the concepts are substantially described with reference to glucose sensors, with, however, other embodiments also being possible as an alternative or in addition thereto. By way of example, the subcutaneous sensor may, as illustrated above, in principle be embodied in accordance with the prior art and may for example have at least one test chemical for detecting the at least one analyte. By way of example, a test chemical may be contained, which changes at least one physically and/or chemically detectable property, for example an electrochemically measurable property and/or an optically measurable property, if the at least one analyte is present. Accordingly, the subcutaneous sensor may, for example, be embodied as an electrochemical sensor. In respect of possible test chemicals, reference can be made to the prior art. The subcutaneous sensor may accordingly for example comprise two or three or more electrodes, by means of which e.g. the at least one analyte can be detected quantitatively and/or qualitatively by electrochemical means. These at least two, preferably three or more, electrodes may for example be contacted, preferably outside of the body tissue, by means of corresponding electrical contacts and may be connected to e.g. the above-described measuring device and/or the actuation and/or evaluation device.

Alternatively, or in addition thereto, the subcutaneous device may also comprise other devices. By way of example, the subcutaneous device may comprise at least one therapeutic function and be embodied accordingly in order to carry out or at least support this therapeutic function. By way of example, the subcutaneous device may for this purpose comprise at least one actuator, for example an electrical and/or mechanical and/or thermal actuator, which acts directly or indirectly on the body tissue and/or a bodily fluid and/or the subject. In another alternative or in addition thereto, the actuator may also be embodied to carry out a medication function. Thus, at least one medicament and/or a differently formulated substance may for example be emitted to the body tissue and/or the subject by means of the subcutaneous device. Various embodiments or combinations are possible, for example subcutaneous devices that combine diagnostic and therapeutic functions. In the following text, reference is substantially made to subcutaneous devices in the form of strip-shaped subcutaneous sensors, for example strip-shaped, subcutaneous electrochemical sensors, for detecting at least one analyte. However, in principle other embodiments are also possible, for example wire-shaped embodiments.

The insertion device comprises at least one such subcutaneous device, which can be implanted or inserted into the body tissue. Furthermore, the insertion device comprises at least one insertion aid, by means of which the subcutaneous device can be inserted. Here, an insertion aid is understood to mean a device that serves the purpose of inserting the subcutaneous device and which can be removed again from the body tissue after the insertion. The insertion aid can be removed directly after inserting the subcutaneous device into the body tissue. The insertion aid can be designed such that the latter merely remains temporarily in the body tissue, for example for a duration of a few milliseconds to a few seconds, for example for at most 60 seconds, preferably for at most 30 seconds and particularly preferably for at most 10 seconds or less. In contrast thereto, the subcutaneous device may remain in the body tissue for a number of minutes, preferably for at least a number of hours and particularly preferably even for a number of days or even weeks.

The insertion aid comprises at least one substantially rigid base body for insertion into the body tissue. By way of example, the substantially rigid base body may be shaped like a needle, i.e. have an elongate shape with a longitudinal extent that significantly exceeds the lateral dimensions of the rigid base body, for example by a factor of 10, preferably by at least a factor of 100 or more. The rigid base body preferably has an integral design but may in principle also have a multipart design. The rigid base body may, as will be explained in more detail below, preferably have at least one insertion tip, by means of which the insertion aid can be introduced into the body tissue. By way of example, the insertion tip can penetrate a skin surface of the subject and/or the body tissue. By way of example, the insertion tip may be embodied as a polished, sharp-edge insertion tip or else as a rounded insertion tip. Atraumatic insertion tips are particularly advantageous. Here, a substantially rigid base body is understood to mean a body, or generally an element, which does not change its external shape, or only makes insubstantial changes thereto, in the case of usual forces that occur during the insertion procedure. In particular, the rigid base body should not, or only insubstantially, change its shape under the influence of its own weight. By way of example, the rigid base body can accordingly be produced from a rigid material, preferably a biocompatible material, for example a metallic material, preferably stainless steel, and/or ceramic material and/or rigid plastic. Combinations of different materials are also possible. In the following text, the rigid base body is also referred to as an insertion needle, without restricting further possible embodiments.

The insertion device is embodied to generate an adjustable holding force between the base body of the insertion aid and the subcutaneous device, for example between the insertion needle and the subcutaneous sensor. Here, an adjustable holding force is understood to mean a force that acts between the subcutaneous device and the base body and is adjustable in terms of its magnitude and/or direction. More particularly, said holding force can be adjusted by the insertion device itself. In particular, the holding force can have a force component perpendicular to a connecting line between the base body and the subcutaneous device. By way of example, the base body and the subcutaneous device may at least in part have an elongate design, with axes of longitudinal extent that are for example arranged in parallel. In this case the adjustable holding force may for example have a component perpendicular to these axes of longitudinal extent.

The insertion device is designed to set different holding forces during the insertion and after the insertion. Hence, the insertion device is designed such that the holding force is set during the insertion such that the subcutaneous device is held against the base body. Furthermore, the insertion device is embodied to set the holding force after the insertion such that the subcutaneous device is detachable from the base body. This change from at least a first holding force acting during the insertion to at least a second holding force, which differs from the first holding force and acts after the insertion, can for example take place automatically by means of the insertion device. By way of example, the insertion device can for this purpose have a control, which can undertake this change from the first holding force to the second holding force, for example in a continuous, incremental or step-wise fashion. By way of example, the control can comprise an electronic control and/or control by a data processing device and can, e.g. wholly or partly, be integrated in the insertion aid and/or in another part of the insertion device. By way of example, this control may be held in a reusable part of the insertion device, whereas the transcutaneous device may for example be wholly or partly embodied as a disposable or at least comprise such a disposable. However, the transcutaneous device may also comprise one or more reusable parts. As an alternative to undertaking the change from the first holding force to the second holding force, or in addition thereto, the change from the first holding force to the second holding force may also for example be triggered by a user, for example by actuating at least one actuation element, for example a trigger button, and/or by simple withdrawal of the insertion aid from the body tissue.

Here, "is detachable from the base body" is understood to mean a state in which the holding force no longer, or merely in a reduced amount, holds the subcutaneous device against the base body. For this purpose, the holding force may in terms of its magnitude and/or direction for example be such that it can easily be overcome, for example by frictional forces on the body tissue, and so the subcutaneous device remains at least partly within the body tissue when the insertion aid is withdrawn from the body tissue. Alternatively, the holding force may also be set completely to zero. In another alternative, the holding force may be such that the subcutaneous device is repelled from the base body.

In respect of its magnitude and/or direction, the holding force can in particular be such that it prevents, at least to a large extent, a spatial displacement between the subcutaneous device and the base body in an insertion direction during the insertion. By way of example, if the base body and the subcutaneous device or the inserted part of the subcutaneous device are oriented substantially parallel to one another during the insertion, for example by the axes of longitudinal extent thereof not deviating from one another by an angle of no more than 10°, preferably of no more than 5°, the holding force may during the insertion for example be such that it at least counteracts a spatial displacement of the base body and the subcutaneous device relative to one another in a direction parallel to the axes of longitudinal extent thereof. As a result, the proposed insertion device differs to e.g. the grippers disclosed in PCT Publication No. WO 03/080169, which still allow a displacement parallel to the axes of longitudinal extent thereof. Moreover, these grippers do not have two different holding forces during the insertion and after the insertion.

The change, i.e. the adjustment of the holding forces during the insertion and after the insertion, may take place continuously or else e.g. stepwise or discontinuously. Provision can also be made for more than two different holding forces during different phases of the insertion and after the insertion. In the process, the holding force need not necessarily be adjusted monotonously in one direction, but may for example also comprise non-monotonous adjustments. The holding force may in particular comprise a non-mechanical holding force, i.e. not a holding force that is caused by e.g. a form fit or an interlock. Various options for generating such an adjustable holding force are in principle known from the prior art and are also usable within the scope of the present insertion device, even in, in principle, arbitrary combination.

In a first embodiment, the holding force comprises an electrostatic holding force. By way of example, such electrostatic holding forces can easily be produced and adjusted by means of two or more electrodes to which appropriate potentials can be applied. Accordingly, merely one or more of the potentials of the electrodes have to be adjusted in order to set or adjust the holding force. Accordingly, the base body can for example have at least a first electrode, wherein the subcutaneous device has at least a second electrode. In principle, an embodiment with more than one first electrode and/or with more than one second electrode is also possible. The first electrode and/or the second electrode may be provided as separate electrodes in the base body or the subcutaneous device, but they can also have a large-area design and for example form relatively large components of the base body or the subcutaneous device. In particular, the entire base body can, for example, be embodied as first electrode, for example by being embodied entirely as a metallic base body to which an appropriate potential may be applied. In general, the insertion device can be designed to apply different electric potentials to the first electrode and the second electrode. Accordingly, at least one potential difference, i.e. a voltage, is formed between the first electrode and the second electrode. As a result of this electric potential difference an electrostatic force acts between the first electrode and the second electrode, which electrostatic force can cause an attraction between the base body and the subcutaneous device or a repulsion between the base body and the subcutaneous device. The magnitude and direction of this electrostatic force may for example be adjusted, accordingly and to a certain amount, by the electrode geometries and/or optionally by materials situated between the electrodes and/or by the potential difference. By way of example, the insertion device can have at least one voltage source, which can generate the different electric potentials or the potential difference between the first electrode and the second electrode. In order to generate different holding forces, it is for example possible to adjust the magnitude and/or direction of this potential difference.

In principle, one or more insulators may in the process be arranged between the first electrode and the second electrode. This at least one insulator via the dielectric constant thereof for example influences the holding force and it may for example comprise at least one dielectric material. The at least one insulator may for example be a component of the insertion aid and/or may also be a component of the subcutaneous device. By way of example, the at least one insulator may comprise at least one ceramic insulator and/or at least one plastic insulator. The at least one insulator can for example prevent direct contact between the first electrode and the second electrode, which direct contact could lead to a short circuit. Furthermore, the direction and/or magnitude of the holding force can be influenced by the at least one insulator.

At least one of the electrodes, i.e. the first electrode and/or the second electrode, may be wholly or partly covered by at least one additional insulator in a preferred embodiment of the invention. By way of example, at least one region of the first electrode and/or second electrode, which is arranged within the body tissue when the insertion device and/or the subcutaneous sensor is introduced into the body tissue, may be wholly or partly covered by the at least one additional insulator. Particular preference is given to the at least one first electrode being wholly or partly covered by the at least one additional insulator. In particular, the at least one first electrode can be screened and/or insulated, for example electrically screened and/or insulated, from the body tissue, for example the interstitium, by the at least one additional insulator. The at least one additional insulator may for example comprise one or more insulation layers, for example one or more organic and/or inorganic insulating layers. The at least one additional insulator may also be wholly or partly combined with the aforementioned insulator, which via its dielectric constant influences the holding force. By way of example, the at least one additional insulator can wholly or partly cover the insertion needle, preferably at least in the region in which the latter is implanted in the body tissue. If the subcutaneous sensor has a mount, more particularly a flexible mount, (this will be explained in more detail below) the thickness of the mount should preferably significantly exceed the thickness of the additional insulator, for example by at least a factor of 2, preferably by at least a factor of 5 and particularly preferably by at least a factor of 10.

As an alternative to using an electrostatic holding force, or in addition thereto, the holding force may in principle also comprise a magnetic holding force. Such a magnetic holding force, which should be an adjustable holding force, may for example be generated by using at least one permanent magnet and/or at least one electromagnet or a combination of such magnets. Such adjustable magnetic holding forces are known from e.g. magnetic switches. By way of example, in the case of electromagnets, the magnetic holding force may be adjusted by adjusting a current, for example by adjusting a current direction and/or adjusting a magnitude of the current. Alternatively, or in addition thereto, the magnetic holding force can be adjusted in the case of e.g. permanent magnets by, in particular, mechanically displacing the at least one permanent magnet. Such principles, in which switching is brought about by means of permanent magnets, are in principle known from the prior art in the form of magnetic switches. A combination of one or more permanent magnets with one or more electromagnets is also feasible. The use of at least one electromagnetic holding element is particularly preferred on account of the simple control. Accordingly, the insertion aid and/or the subcutaneous device can comprise at least one electromagnetic holding element that is embodied to generate a magnetic field. By way of example, the electromagnetic holding element may comprise at least one printed conductor loop and/or a coil. In the process, the electromagnetic holding element may for example be arranged on or in the insertion aid or—alternatively or additionally—in or on the subcutaneous device. If only one of the two elements, i.e. either the insertion aid or the subcutaneous device, is embodied with an electromagnetic holding element for generating a magnetic field, the respective other element, i.e. the subcutaneous device or the insertion aid, may comprise a corresponding counter element, for example likewise a magnetic holding element (e.g. a permanent magnetic holding element and/or an electromagnetic holding element) or a passive element such as e.g. a soft-magnetic element and/or a ferromagnetic element, which can interact with the electromagnetic holding element. If provision is made for at least one electromagnetic holding element, preferably in the insertion aid, the insertion device can for example have at least one current source for generating an adjustable current that can be fed into the at least one electromagnetic holding element. By way of example, this current source can be embodied as an adjustable current source such that the current can be set in terms of its magnitude and/or direction.

In a further alternative to the above-described electrostatic and/or magnetic principles for generating the adjustable holding force, or in addition thereto, use can be made of further principles for generating the adjustable holding force. By way of example, it is possible to influence adhesion forces between the base body and the subcutaneous device in a targeted fashion, e.g. once again by electric fields and/or in a different electric and/or magnetic fashion. In particular, the insertion device can be designed to influence an electric charge carrier density and/or an electric conductivity in the region of at least one adhesion surface of the insertion aid and/or subcutaneous device. Here, an adhesion surface is understood to mean a surface of the insertion aid and/or subcutaneous device, which is arranged adjacent to the respective other element, for example by the subcutaneous device resting on the adhesion surface of the insertion aid or vice versa. Hence, the adhesion surface can be a component of the insertion aid or a component of the subcutaneous device. Alternatively, the insertion aid and the subcutaneous device can have such adhesion surfaces. By way of example, there may be at least one adhesion force between the subcutaneous device and the insertion aid, which adhesion force can be promoted and/or caused by adhesive materials such as e.g. adhesives and/or other materials, for example adhesive organic materials. Furthermore, as an alternative to the aforementioned materials, or in addition thereto, sugars or salts, e.g. in the form of sugar solutions and/or salt solutions, are to be mentioned here as adhesive materials in an exemplary fashion, which solutions are dissolved, e.g. automatically, in the case of a change in the water content of their surroundings during the insertion. In these cases, or else in other cases, the adhesion force between the subcutaneous device and the insertion aid can be influenced in a targeted fashion by virtue of the fact that the electric charge carrier density and/or the electric conductivity is influenced in the region of the at least one adhesion surface of the insertion aid and/or subcutaneous device. By way of example, this can be brought about using a field effect. By means of a field effect, which is for example utilized in a field-effect transistor, it is possible to influence the charge carrier density and/or the electric conductivity in the region of the at least one adhesion surface, for example by adjusting a voltage at at least one electrode, for example a switching electrode or a so-called gate electrode. The at least one adhesion surface can accordingly have e.g. a semiconducting material, for example an organic and/or an inorganic semiconducting material. Accordingly, materials that can be used e.g. in organic field-effect transistors can be used at least in the vicinity of the adhesion surface. By way of example, these materials can be conductive or semiconducting organic materials, more particularly conjugated polymers or other conjugated organic materials, i.e. materials with a conjugated π-electron system. Examples of such organic conductive or semiconducting materials are polyacetylene, polyaniline, polythiophene, polyparaphenylene or other organic materials with an extended π-electron system. The at least one adhesion surface can accordingly comprise at least one field-effect transistor, for example a MOSFET, for example an organic field-effect transistor, wherein the semiconductor material of the field-effect transistor respectively faces the other element. By way of example, if the adhesion surface is a component of the insertion aid, the semiconducting material should face the subcutaneous device or the corresponding adhesion surface thereof. If the field-effect transistor is a component of the subcutaneous device, the semiconductor material thereof should face the insertion aid. Combinations of a plurality of field-effect transistors are also possible.

The aforementioned examples for generating an adjustable holding force, which examples can also be used in combination, are merely possible examples of how such an adjustable holding force can be generated and adjusted. In principle, the prior art has disclosed different other options for generating a force between the insertion aid and the subcutaneous device, which force is preferably non-mechanical, which force preferably acts contactlessly and which force is adjustable.

The insertion aid can in particular have a support surface for the subcutaneous device to rest on during the insertion. By way of example, this support surface may comprise or form the above-described at least one optional adhesion surface of the insertion aid. More particularly, the support surface may be embodied as a substantially planar support surface in contrast to e.g. the known hollow needles for inserting a subcutaneous sensor. In particular, the insertion aid may be embodied such that the latter does not surround the subcutaneous device such that the subcutaneous device can be removable independently of the insertion aid without the holding force perpendicular to the direction of longitudinal extent of the insertion aid.

On a side opposing the support surface, the insertion aid may have a profile, more particularly one of the following profiles: a polygonal profile, more particularly a triangular profile or a trapezoidal profile; a round profile, more particularly a circular-arc-shaped profile. A profiling, for example of the described type, can increase the stability of the insertion aid during the insertion into the body tissue, particularly when said insertion aid is at least in part embodied as an insertion needle. At the same time, there can be a reduction in the profile of the puncture channel, and the sense of pain can be reduced. By way of example, the insertion needle can have at least one insertion tip. Here, an insertion tip is understood to mean a sharp-edged or pointed element, wherein use can be made of both polished tips and tips with a round cross section, more particularly atraumatic insertion tips. Particular preference is given to the insertion aid to have at least one raise in the region of the insertion tip, with the raise at least partly covering the subcutaneous device during the insertion such that force acting on the subcutaneous device is at least reduced during the insertion of the insertion aid with the subcutaneous device. On the side facing the subcutaneous device, the raise can have a ramp such that it is easier to remove the subcutaneous device from the insertion aid, e.g. by gliding over said ramp, when the insertion aid is removed from the body tissue. By way of example, the raise can directly adjoin the support surface or adjoin it via the ramp, the support surface for example being the substantially planar support surface which for example may contain a flattening on an otherwise e.g. round insertion needle.

As illustrated above, the insertion device thus comprises at least one subcutaneous device and at least one insertion aid, wherein an adjustable holding force can be generated between these elements. Thus, in addition to the insertion device in one or more of the above-described embodiments, an insertion aid and a subcutaneous device are furthermore proposed, which can in particular be embodied to be used in the insertion device as per one or more of the above-described embodiments. Accordingly, reference can at least largely be made to the description above. However, in principle the insertion aid and the subcutaneous device can also be used in other insertion devices, in particular as long as the described principle of generating an adjustable holding force is implemented.

As illustrated above, the proposed insertion aid serves for at least partly inserting a subcutaneous device into body tissue. The insertion aid has at least one substantially rigidly designed base body for insertion into the body tissue, more particularly at least one insertion needle. By way of example, this insertion needle can be embodied as a solid needle, i.e. without a cavity. For the optional generation of a support surface as per the description above, the insertion needle can for example comprise a flattening. The insertion aid is designed to interact with the subcutaneous device such that an adjustable holding force can be generated between the base body and the subcutaneous device. By way of example, the insertion aid may, for this purpose, comprise at least a first holding element. By way of example, the subcutaneous device can accordingly comprise at least a second holding element and/or be embodied to interact with the first holding element in a different fashion. As illustrated above, the at least one first holding element of the insertion aid may be e.g. an electrostatic and/or a magnetic, more particularly electromagnetic, first holding element and/or a first holding element based on a change in a charge carrier density and/or a conductivity in the region of an adhesion surface of the insertion aid. Combinations are also possible. In respect of further embodiments, reference can be made to the description above. By way of example, the holding element can be connected to a control via appropriate feed lines in the insertion aid such that the holding force can be adjusted in a targeted fashion. In respect of further possible embodiments, reference can be made to the description above and there in particular to features relating to the insertion aid.

The proposed subcutaneous device is suitable for insertion into body tissue, wherein the subcutaneous device can be wholly or partly inserted into the body tissue, for example in a transcutaneous fashion. In particular, the subcutaneous device can have an implantable part and a non-implantable part. In particular, the subcutaneous device can be wholly or partly embodied as a subcutaneous sensor or can comprise a subcutaneous sensor, more particularly a subcutaneous sensor for detecting at least one analyte, for example in the body tissue and/or in a bodily fluid. However, as illustrated above, other embodiments of the subcutaneous device are also possible, for example embodiments in which the sensor detects at least one other physical and/or chemical property of a subject, and/or embodiments in which the subcutaneous device comprises at least one medication device and/or at least one actuator for acting on the body tissue and/or the subject. The subcutaneous device can, as illustrated above, comprise at least one implantable part. This implantable part preferably has a wholly or partly flexible design, and so it can deform during usual movements within the body tissue. Accordingly, the subcutaneous sensor can for example have a mount, more particularly a flexible mount, for example a strip-shaped flexible mount and/or a tubular flexible mount. By way of example, the mount can comprise a plastics material and/or a paper material and/or a ceramic material as a flexible material, wherein laminate materials are also possible. The mount can hold one or more functional elements. By way of example, as illustrated above, one or more test fields and/or electrodes of a subcutaneous sensor can be held on the mount and/or in the mount, for example for detecting the at least one analyte in the bodily fluid or body tissue by electrochemical and/or optical means. In this respect, reference can be made to conventional test elements from the field of diagnostics, which test elements can for example be used to detect at least one analyte in a bodily fluid; reference can also be made to the prior art cited above. Furthermore, the subcutaneous device can for example comprise one or more feed lines, which can for example be routed to a region outside of the body tissue via the mount in order to be connected there to e.g. a control. By way of example, the mount can be embodied as a disposable and can be connected to e.g. a reusable.

The subcutaneous device can in particular be used for use in an insertion device in one or more of the above-described embodiments. The subcutaneous device is accordingly designed to interact with a base body of an insertion aid for insertion into the body tissue such that an adjustable holding force can be generated between the base body and the subcutaneous device. By way of example, this base body may be the above-described, substantially rigidly designed base body of the insertion aid. As illustrated above, the subcutaneous device may for this purpose comprise, e.g. in an implantable part, at least a second holding element, which can interact with the base body of the insertion aid such that the adjustable holding force can be generated. By way of example, this second holding element can interact with a first holding element of the insertion aid and/or with the entire base body of the insertion aid. As illustrated above, the second holding element can be based on, for example, an electrostatic principle, a magnetic principle, more particularly an electromagnetic principle, and/or the principle of adjusting a charge carrier density and/or a conductivity in the region of at least one adhesion surface of the subcutaneous device. By way of example, this adhesion surface can be a surface of the subcutaneous device, which rests on the above-described support surface of the insertion aid during the insertion. However, alternatively or additionally, it is also possible to use other functional principles for generating an adjustable holding force.

The insertion device according to these teachings, the insertion aid and the subcutaneous device have a number of advantages over known devices of the aforementioned types. By way of example, this can realize a controllable insertion needle, by means of which a subcutaneous device, e.g. a sensor, can be implanted in a targeted and reliable fashion. In the process, use can be made of a physical connection between insertion needle and sensor for inserting e.g. a continuously measuring sensor. As illustrated above, use can be made of different physical mechanisms, for example electrostatic charging, which occurs by connecting an electric field to the insertion needle and the sensor, or magnetism or a targeted adjustment of adhesion properties of an adhesion surface. The latter can, as illustrated above, for example be brought about by applying an electric field, which can align conductive organic polymers such that their adhesion properties at boundaries change and/or that there is a change in a charge carrier density and/or conductivity at the adhesion surface. The aforementioned principles or other principles may have the following in common: there can be targeted adjustment of the adhesion of insertion needle to sensor or insertion aid to subcutaneous device by varying physical properties of the group composed of these two objects. Hence, the idea of these teachings differs from the prior art, in which use is made of substantially rigid insertion aids or insertion aids whose own properties can be adjusted slowly. With respect to the above-described WO 03/080,169, the idea disclosed herein differs in that the holding force can be adjusted in a targeted fashion and in that, for example during the insertion, a holding force can also be exerted onto the subcutaneous device, which holding force can act along an insertion direction, i.e. parallel to the axes of longitudinal extent of the insertion aid and/or subcutaneous device. By way of example, this can also prevent a displacement of the subcutaneous device on or in the insertion aid during the implantation or a kinking of the same.

By means of the described insertion device, insertion aid and/or subcutaneous device, it is possible to apply, in particular, a subcutaneous, flexible sensor or another type of subcutaneous device into the body tissue, for example into the skin, by minimally invasive means such that the puncture profile is minimal. To this end, the subcutaneous device and/or the implantable part thereof can be stiffened during the introduction (insertion). When the insertion aid is removed, the subcutaneous device may remain unchanged in its intended shape. Hence, the leaving-behind of the subcutaneous device in the tissue when the insertion aid is removed can take place at a defined time, i.e. in a controlled fashion. In particular, a "trigger mechanism" can set a defined time at which the subcutaneous device is released from the insertion aid, for example by influencing the adjustable holding force in a targeted fashion.

In particular, this can be developed such that the subcutaneous device, which, as illustrated above, preferably has a wholly or partly flexible design, e.g. as a flexible sensor, is supported in a temporally defined fashion by the insertion aid during the insertion, e.g. during the puncturing. This can take place in a controlled fashion, for example by a control that influences the holding force in a targeted fashion. The insertion aid can for example have a flat structure, which has a contour that is similar to the subcutaneous device or the implantable part thereof, e.g. the sensor, and supports the subcutaneous device. As a result, the subcutaneous device, e.g. the flexible sensor, cannot deviate from its straight insertion movement as a result of insertion forces. In the process, the flexible subcutaneous device can nestle against a rigid flat insertion needle with a similar contour to the sensor. By way of example, this nestling can, as illustrated above, be generated by one or more adjustable holding forces, for example by electrostatic, electromagnetic or controllable adhesion forces or sticking forces. The terms "adhering" and "sticking" are in this case used largely synonymously within the present scope. A combination of the aforementioned holding forces and/or other holding forces, which can be adjusted, is also possible. The controlled nestling between the insertion device and the subcutaneous device can more particularly bring about that the holding force of the subcutaneous device, e.g. the sensor, on the insertion aid, e.g. the insertion needle, exceeds the sliding forces during the insertion, which sliding forces act on the subcutaneous device as a result of the skin or the body tissue. Once the subcutaneous device, e.g. the sensor, has reached the final position, the holding force can be adjusted in a targeted fashion, for example be switched off in a targeted fashion or even reversed (such that there is repulsion for example), such that the subcutaneous device remains in the final position, i.e. in an at least partly implanted position, when the insertion aid is removed from the body tissue. By way of example, this can be brought about by virtue of the fact that friction between the subcutaneous device and the insertion aid is reduced and/or the subcutaneous device is repelled from the insertion aid such that the insertion aid can easily be withdrawn from the body tissue and without the subcutaneous device.

The insertion aid, more particularly the insertion needle, can be as wide as the subcutaneous device, more particularly an implantable part of the subcutaneous device, e.g. a sensor, and can accordingly have a relatively thin design. This can ensure that the puncture profile is only minimally larger than the sensor profile on its own and is in any case smaller than that of a hollow needle. Accordingly, preference is given to the insertion aid, more particularly the insertion needle, having a maximum extent perpendicular to the insertion direction that does not exceed, or only slightly exceeds, the maximum extent of the implantable part of the subcutaneous device, for example by at most 50%, preferably by at most 20% and particularly preferably by at most 10%. By way of example, this can be ensured by virtue of the fact that the implantable device, for example a flexible sensor, completely covers the support surface, at least in terms of the width thereof, i.e. perpendicularly to the insertion direction. However, in principle the subcutaneous device can also have a wholly or partly rounded design, for example with a rounded, angled or curved profile in a sectional plane perpendicular to the direction of insertion. However, a substantially planar design in this sectional plane is preferred.

The above-described targeted influencing of adhesion properties of an adhesion surface by influencing the charge carrier density and/or conductivity in the region of this adhesion surface also opens new application options, more particularly in the use of organic semiconducting and/or conducting materials, such as e.g. conjugated polymers or low-molecular organic substances with conjugated π-electron systems. Thus, by way of example, polymer-electronic materials can be produced and used in a cost-effective fashion, even in industrial-scale mass processes. This allows e.g. subcutaneous devices, more particularly implantable sensors, to be produced in a cost-effective and flexible fashion. By way of example, polymer-electronic materials can be optimized and developed in a targeted fashion to new, specific properties. Thus, for example, it is conceivable that a polymer adjusts its alignment, and hence its local charge carrier density and/or its charge carrier density and/or conductivity, in a targeted fashion by applying an electric voltage. As a result, adhesion properties can be set by targeted control of adhesion forces.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
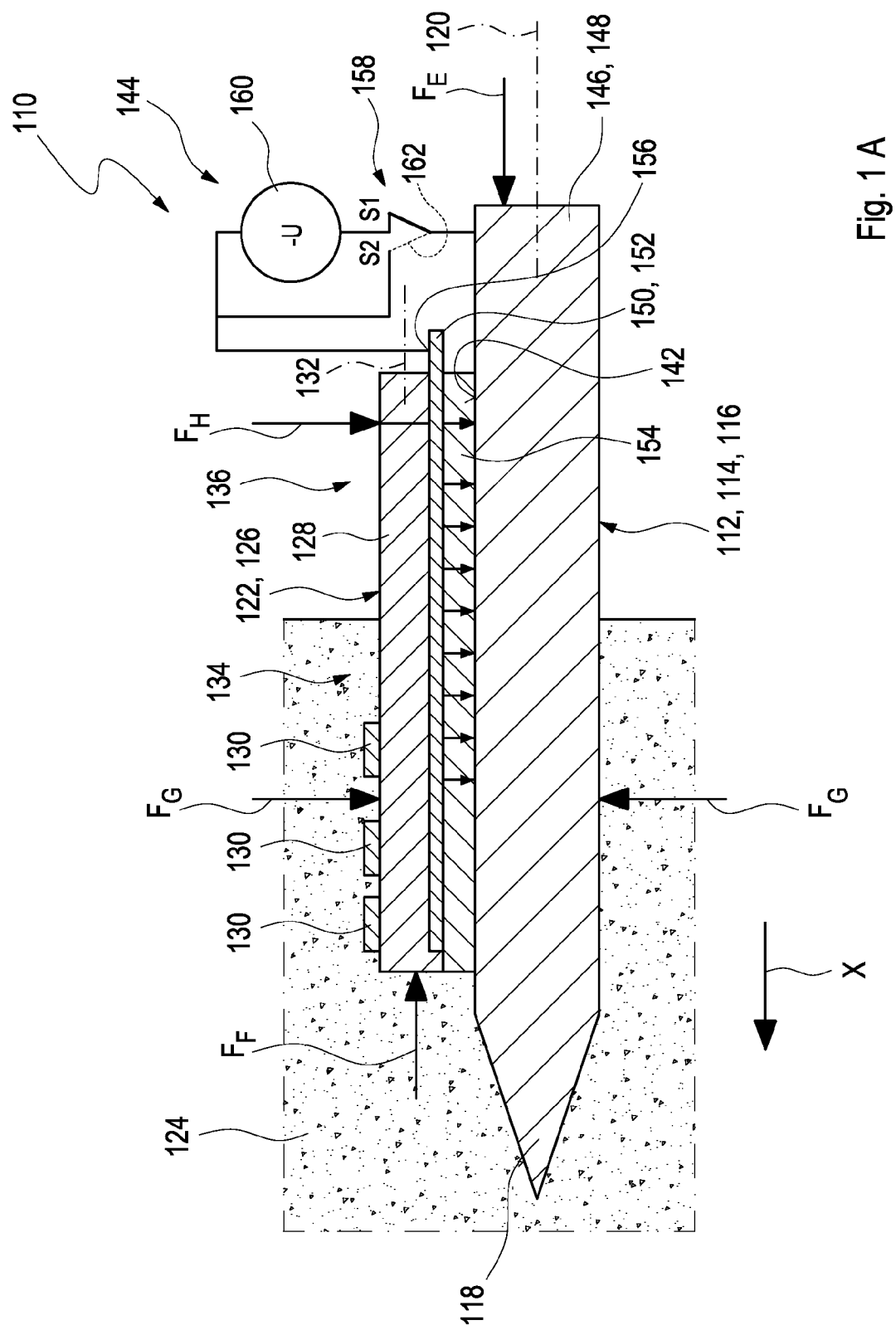
FIGS. 1A and 1B are different illustrations of a first exemplary embodiment of an insertion device with an electrostatic holding force.
Figure 1:
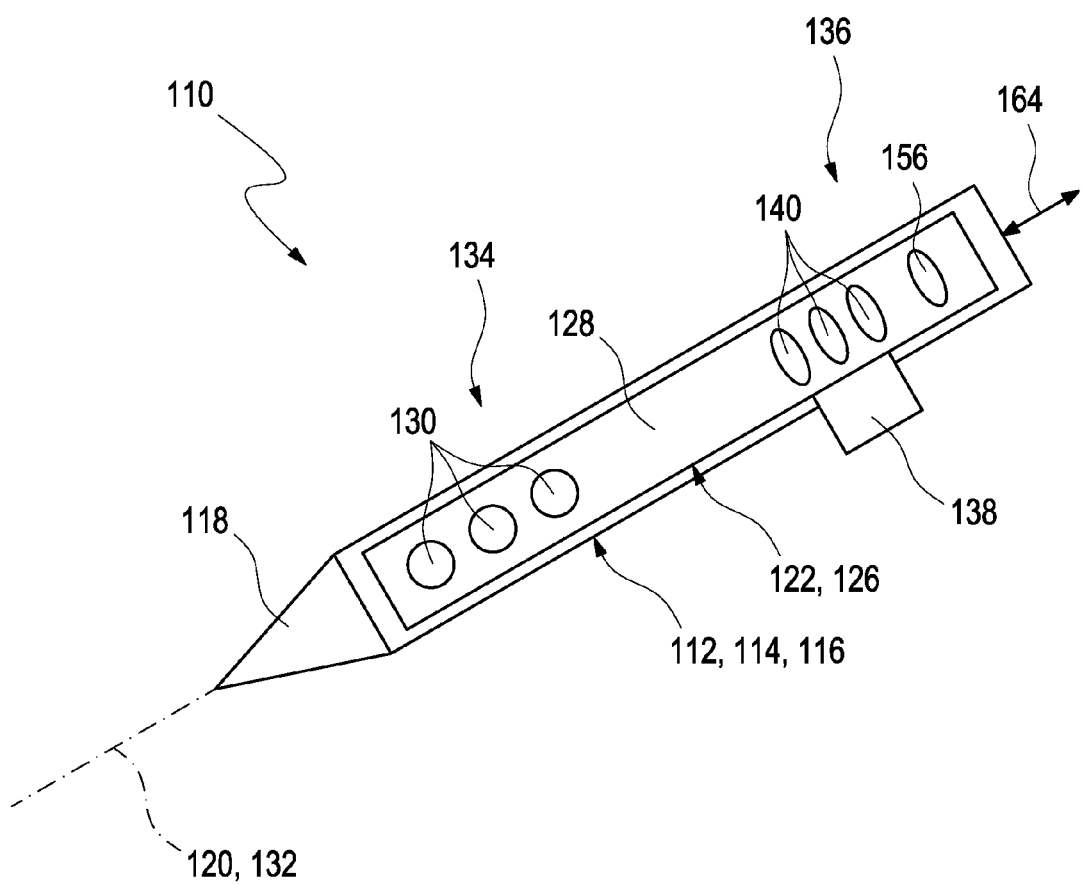
FIG. 1C illustrates a modification of the exemplary embodiment of the insertion device illustrated in FIGS. 1A and 1B.

FIGS. 1A and 1B show a first exemplary embodiment of an insertion device 110 in various illustrations. In the process, FIG. 1A shows a sectional illustration in a sectional plane parallel to a puncture path denoted by "x", and FIG. 1B shows a plan view of the insertion device 110.

Figure 3:
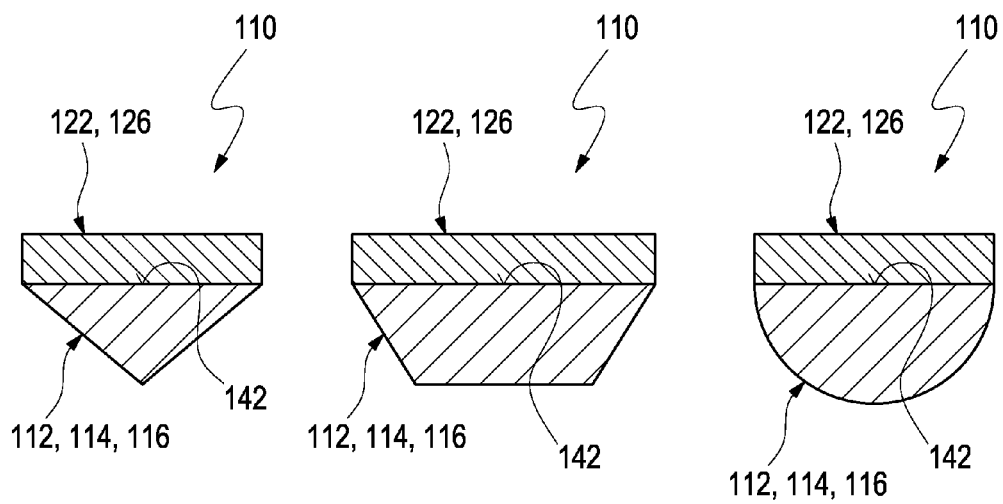
FIGS. 3A to 3C show different profiles of an insertion device.
Figure 4:
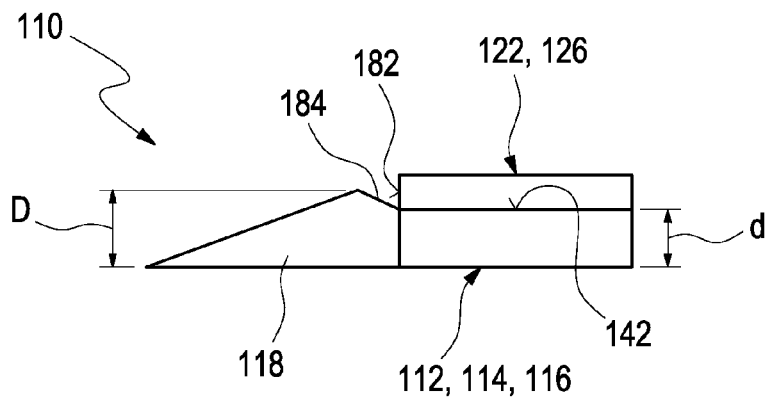
FIG. 4 shows an insertion device with a raised insertion tip.

The insertion device 110 comprises an insertion aid 112 with a substantially rigidly embodied base body 114. Here, the base body 114 is embodied as an insertion needle 116, for example in the form of a solid needle, for example a solid needle produced from steel. The insertion needle 116 has an insertion tip 118, which, in an exemplary fashion, is illustrated here with a round tip. However, in principle, other embodiments are also possible, for example the embodiments described below in FIGS. 3A to 4. The insertion needle 116 is embodied as an elongate, rigid base body 114, which substantially extends in the direction of the puncture path x, with an axis of longitudinal extent 120.

The insertion device 110 furthermore has a subcutaneous device 122, which should be inserted into body tissue 124 by means of the insertion device 110. The body tissue 124 is merely illustrated symbolically in FIG. 1A. In the illustrated exemplary embodiment, the subcutaneous device 122 is, in an exemplary fashion, embodied as a subcutaneous sensor 126, which serves to detect at least one analyte in the body tissue 124 or a bodily fluid in the body tissue 124. However, as illustrated above, other embodiments are also possible. The subcutaneous sensor 126 has a mount 128 on which, in the illustrated exemplary embodiment, three sensor electrodes 130 are arranged in an exemplary fashion, for example such that these sensor electrodes 130 face the body tissue 124. Here, the sensor electrodes 130 for example have a circular design, with other geometries also being possible, for example an oval or polygonal geometry. A different number of sensor electrodes is also possible. By way of example, the sensor electrodes 130 can comprise at least one working electrode, at least one counter electrode and at least one reference electrode for detecting at least one analyte in the body tissue 124 and/or in a bodily fluid by electrochemical means. The at least one counter electrode and the at least one reference electrode can also be wholly or partly combined to form a common electrode. The sensor electrodes 130 may, in addition to comprising, e.g. metallic electrodes, furthermore comprise e.g. one or more redox systems and/or enzymes. Such sensor electrodes 130 are in principle known from the prior art from the field of electrochemical analyte detection.

By way of example, the mount 128 has a flexible design and can, for example, comprise a multi-layer design. By way of example, the mount 128 can be wholly or partly produced from a plastics material and/or a paper material and/or a ceramic material and/or a laminate material and can likewise extend along an axis of longitudinal extent 132, which may for example be arranged parallel to the axis of longitudinal extent 120 during the insertion, as illustrated in FIG. 1A. In the process, the subcutaneous device 122 is partly inserted into the body tissue 124, which subcutaneous device has an implantable part 134 and a non-implanted part 136. By way of example, the subcutaneous device 122 may have a holder 138 in the region of the non-implanted part 136, which holder can be identified in FIG. 1B in particular. This holder 138 can for example be used to hold the subcutaneous device 122 or withdraw the latter from the body tissue 124 after use. By way of example, the subcutaneous device 122 can comprise sensor contacts 140, for example respectively one sensor contact 140 per sensor electrode 130, in the region of the non-implanted part 136. By way of example, these sensor contacts 140 can be connected to the sensor electrodes 130 via electrode feed lines (not illustrated in FIGS. 1A and 1B), which are for example situated within a layer of the mount 128, and so the sensor electrodes 130 can be contacted electrically or the potential thereof can be tapped.

In the exemplary embodiment illustrated in FIGS. 1A and 1B, the flexible subcutaneous sensor 126 with the substantially strip-shape design lies flat on a support surface 142 of the insertion aid 112. However, in principle other embodiments are also possible.

An idea of the present insertion device 110 as per the illustrated exemplary embodiment consists of generating an adjustable holding force between the insertion aid 112 and the subcutaneous device 122. To this end, the insertion device 110 has a control 144 in the illustrated exemplary embodiment, which control can for example be a component of the insertion aid 112 and/or can be arranged externally, for example in a reusable part of the insertion device 110. By way of example, the insertion needle 116 in this exemplary embodiment has a metallic design and acts overall as first electrode 146 and hence as first holding element 148. The subcutaneous device 122 in turn has a second electrode 150 as second holding element 152. By way of example, this second electrode 150 in the form of a metallic lamination and/or a flexible copper coating can be applied to the mount 128, and/or can be integrated into the mount 128. Various embodiments are possible. Thus, for example, the insertion needle 116 can, instead of using metals, be wholly or partly coated with organic polymers, which have conductive properties, and thus form a first electrode 146. The use of organic conducting materials as materials of the second electrode 150 is also feasible in the subcutaneous device 122.

The materials of the insertion aid 112 and/or the subcutaneous device 122 preferably have a wholly or partly sterilizable design, for example by means of radiation, more particularly one or more of the following radiations: UV radiation, X-ray radiation, gamma radiation and electron radiation.

The insertion device 110 furthermore has at least one insulator 154 arranged between the first electrode 146 and the second electrode 150. By way of example, this insulator 154 can wholly or partly be a component of the insertion aid 112 and/or can wholly or partly be a component of the subcutaneous device 122. In particular, the insertion needle 116 and/or the subcutaneous device 122 can be provided on all sides with an insulator 154, for example an appropriate coating, in order to avoid short circuits in the tissue.

The first electrode 146 and the second electrode 150 can be connected to the control 144 during the insertion procedure. To this end, the subcutaneous device 122, as can be identified in FIG. 1B for example, can for example comprise a magnetoresistor contact 156, via which a corresponding connection can be made between the control 144 and the second electrode 150, which is for example embodied as a magnetoresistor. Accordingly, it is also possible to connect the insertion aid 112, more particularly the insertion needle 116, to the control 144. This connection may be permanent; however, it can also be wholly or partly severed after the insertion has taken place.

As illustrated in FIG. 1A, the control 144 preferably comprises a switch-over device 158, by means of which a potential difference between the first electrode 146 and the second electrode 150 can be adjusted such that an electrostatic holding force between the subcutaneous device 122 and the insertion aid 112 can be adjusted. In the illustrated exemplary embodiment, the switch-over device 158 is designed for optionally interconnecting the first electrode 146 and the second electrode 150 via a voltage source 160 or via a short-circuit connection 162. Other embodiments, by means of which a potential difference between the first electrode 146 and the second electrode 150 can be adjusted, are also possible. In the illustrated exemplary embodiment as per FIG. 1A, the illustrated switch position, which is denoted by $S_1$ here, brings about an attractive holding force between the subcutaneous device 122 and the insertion aid 112, whereas the switch position $S_2$, illustrated by a dashed line, of the switch-over device 158 would bring about a holding force of 0 or even a repulsion between the insertion needle 116 and the subcutaneous device 122. The voltage source 160 can in particular comprise a direct-current voltage source. Hence, an attractive electrostatic force acts in the switch position $S_1$. The voltage preferably remains applied during the insertion procedure. Before the insertion needle 116 is withdrawn from the body tissue 124, the voltage source 160 is switched off or the switch-over device 158 is brought into the switch position $S_2$. This for example short-circuits the electrodes 146, 150. In this case no holding force acts anymore or the electrodes 146, 150 are repelled from one another as a result of the same potentials. The friction is thus reduced and the insertion needle 116 can easily be withdrawn against the contact pressure of the body tissue 124. By way of example, this can be brought about by means of an appropriate puncturing device and/or retraction device, which can optionally also provide an electrical contact and which is denoted by reference sign 164 in FIG. 1B in a symbolic fashion.

The force ratios of the forces acting on the insertion device 110 are illustrated below. These forces are partly illustrated in FIG. 1A. Here, $F_G$ denotes the force exerted on the insertion device 110 by the tissue, $F_H$ denotes the holding force caused by the electric field, $F_E$ denotes the puncture force during the insertion procedure and $F_F$ denotes the frontal force acting on the subcutaneous device 122 during the insertion procedure.

The following relation holds true for the electrostatic force between two ideal, plate-shaped electrodes 146, 150:

$$F_H = \frac{1}{2} * \frac{\varepsilon_0 \varepsilon_r * A * U^2}{a^2} \tag{1}$$

Here, $\varepsilon_0$ denotes the dielectric constant, which is $8.85*10^{-12}$ As/Vm, $\varepsilon_r$ denotes the relative dielectric constant, which typically lies between 4 and 80 and which is dimensionless, A denotes the effective electrode surface of the electrodes 146 and 150, which can for example lie between 5 and 50 mm², more particularly at 20 mm², a denotes the distance between the electrodes 146, 150, which can for example lie between 10 μm and 100 μm, more particularly at 50 μm, and U denotes the voltage between the electrodes 146, 150, which can for example lie between 1 and 100 volts, more particularly at 10 volts. In the case of the specified values with an area A of 20 mm², a distance a of 50 μm and a voltage of 10 volts, the holding force is approximately 0.3 mN, i.e. it is comparatively low. In order to increase this holding force $F_H$, an increase in the voltage U and/or a reduction in the distance a are suitable.

In order to insert the insertion device 110, more particularly the insertion needle 116 and the subcutaneous sensor 126, the following puncture force $F_E$ must be applied:

$$F_E = \mu_{1,2} {}^*F_G \mu_{3,4} {}^*F_G + F_F.$$

In a simplifying fashion, this relation (2) merely considers the dynamic friction and a static state. Here $\mu_{1,2}$ and $\mu_{3,4}$ denote the coefficients of dynamic friction between the subcutaneous device 122 and the tissue 124 ($\mu_{1,2}$) and between the insertion aid 112 and the tissue 124 ($\mu_{3,4}$).

The following must hold true for the subcutaneous device 122 to adhere to the insertion aid 112 during the insertion procedure:

$$(\mu_{1,2} {}^*F_G + F_F) << \mu_{2,3} {}^*F_H.$$

Here, $\mu_{2,3}$ denotes the coefficient of friction between the subcutaneous device 122 and the insertion aid 112, which, multiplied by the holding force $F_H$, characterizes the frictional force of the subcutaneous device 122 on the insertion aid 112, which frictional force counteracts the subcutaneous device 122 slipping on the insertion aid 112 during the puncturing procedure. If the aforementioned relation (3) is satisfied, and if the insertion needle 116 is sufficiently stiff, the insertion device 110 remains stretched throughout the insertion procedure. Typical coefficients of static friction $\mu_{1,2}$ and/or $\mu_{3,4}$ are of the order of 0.24, for example for brass on wood tissue with an interjacent water film.

Figure 1C:
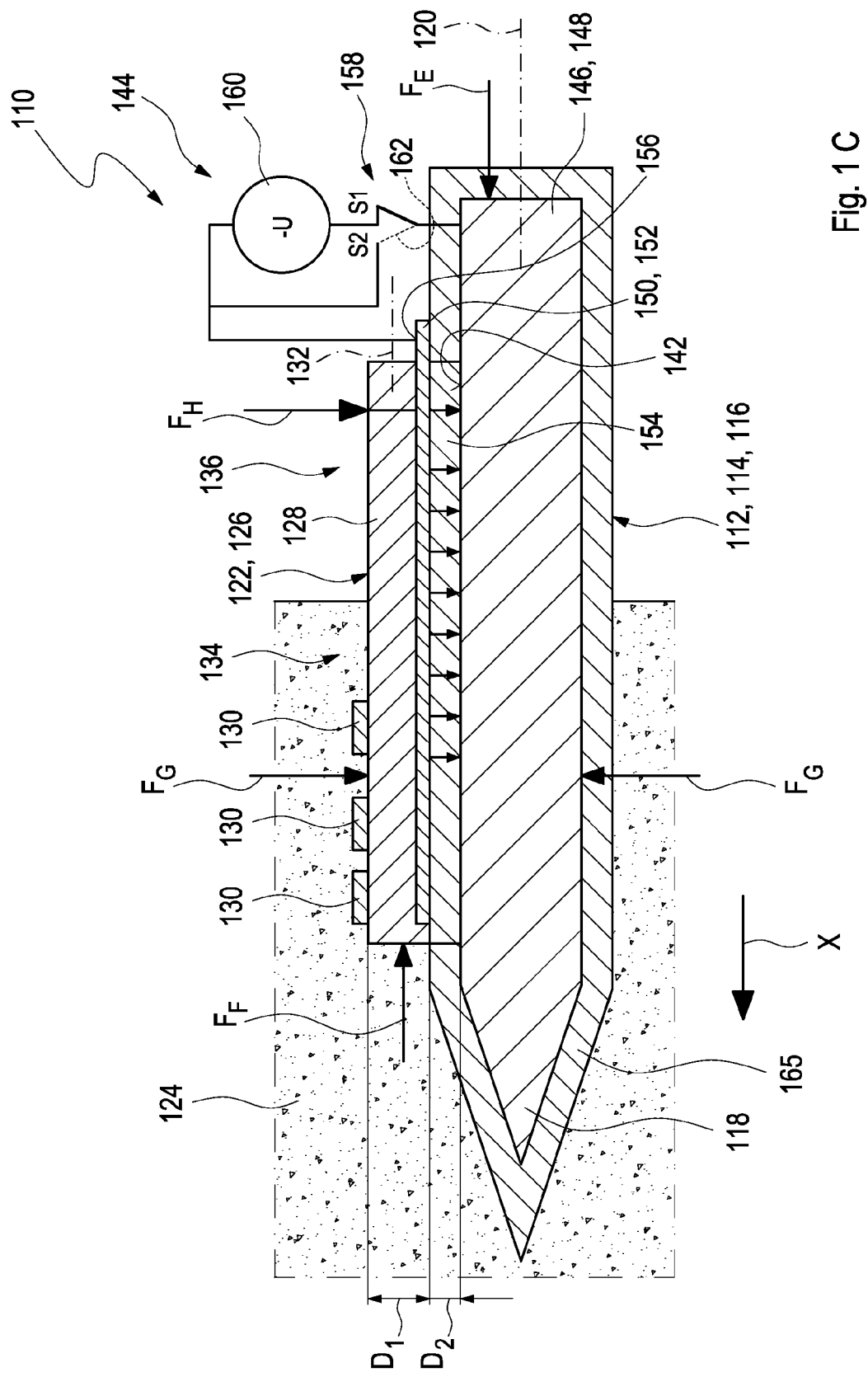

FIG. 1C illustrates a modification of the exemplary embodiment of the insertion device 110 illustrated in FIGS. 1A and 1B. The modification firstly substantially corresponds to the exemplary embodiment in FIGS. 1A and 1B, and so reference can largely be made to the above description of this exemplary embodiment. However, the first electrode 146 is, in addition, optionally wholly or partly covered by an additional insulator 165, e.g. an insulation layer, in the illustrated modification. By way of example, the additional insulator 165 can completely or partly cover the first electrode 146 in the regions that protrude into the body tissue 124, for example into the interstitium, in the implanted state. By way of example, the additional insulator 165 can be embodied as a hermetically sealed electrical insulation. The additional insulator 165 can also be wholly or partly combined with the insulator 154 (which for example acts as a dielectric), for example to form a common insulation coating for the insertion needle 116, or be wholly or partly identical to this insulator 154.

This modification takes account of the fact that in the case of lacking or insufficient insulation of the first electrode 146 from the body tissue 124, the potential of the first electrode 146 could reach the rear side of the mount 128, for example the mount film, via the generally conducting body tissue 124, for example the interstitium. As a result, the field and the action of the force between the first electrode 146 and the second electrode 150 could be weakened or even lifted as a result of the insulator 154 acting as dielectric. This is brought about by virtue of the fact that a second force field is formed, which is directed in the opposite direction. This effect can be reduced or even avoided entirely by the at least partial insulation of the first electrode 146, particularly with respect to the body tissue 124.

The thickness of the mount 128, for example the mount film, is denoted symbolically by $D_1$ in FIG. 1C, whereas the thickness of the additional insulator 165 is denoted by $D_2$. For safeguarding against a faulty insulation of the first electrode 146, the thickness $D_1$ of the mount 128 should where possible be selected to be significantly greater than the thickness $D_2$ of the additional insulator 165. This can reliably ensure that the forming parasitic capacitor and the compensating force resulting therefrom are markedly reduced.

Figure 2:
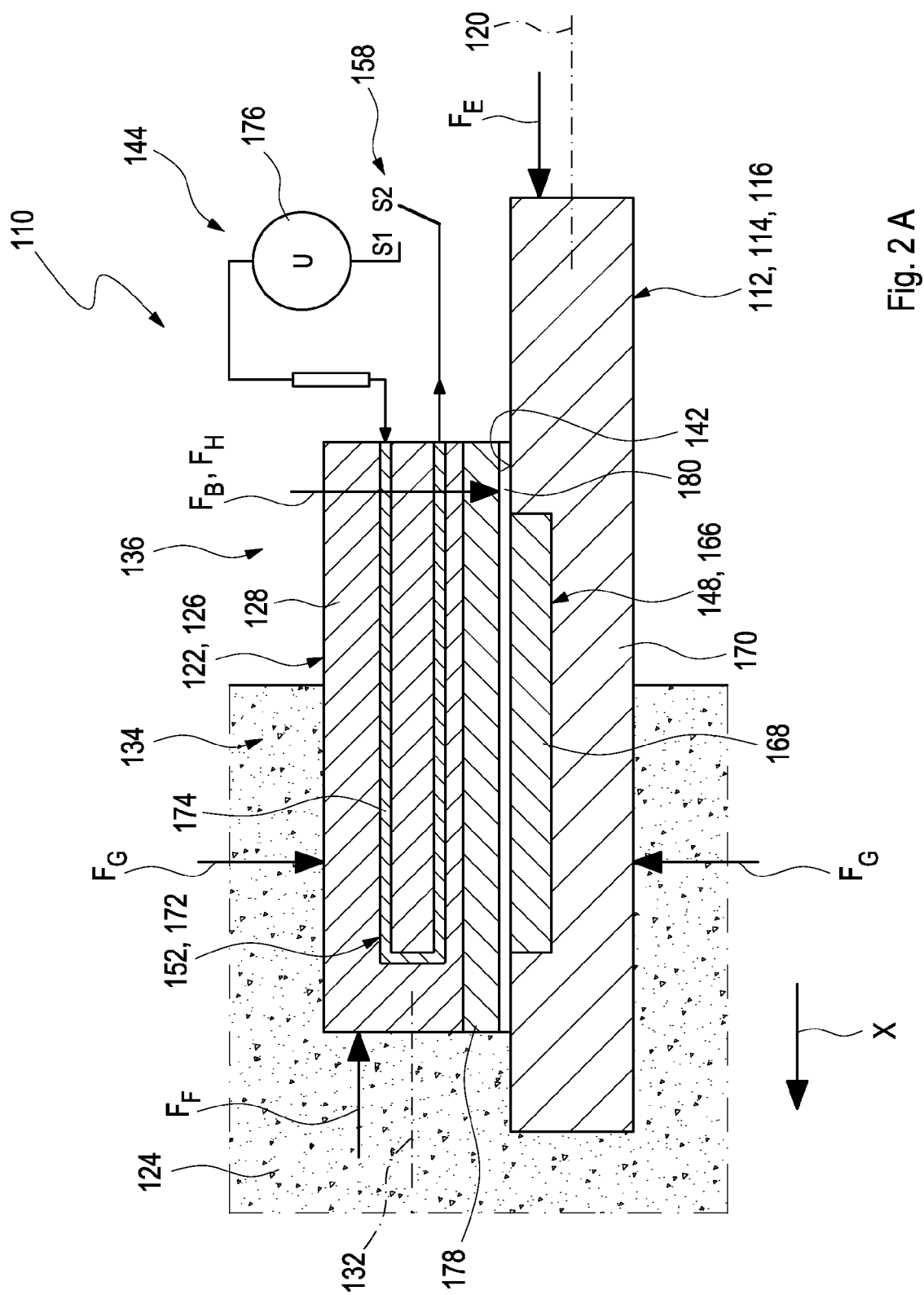
FIGS. 2A and 2B show different views of a second exemplary embodiment of an insertion device with a magnetic holding force.
Figure 2:
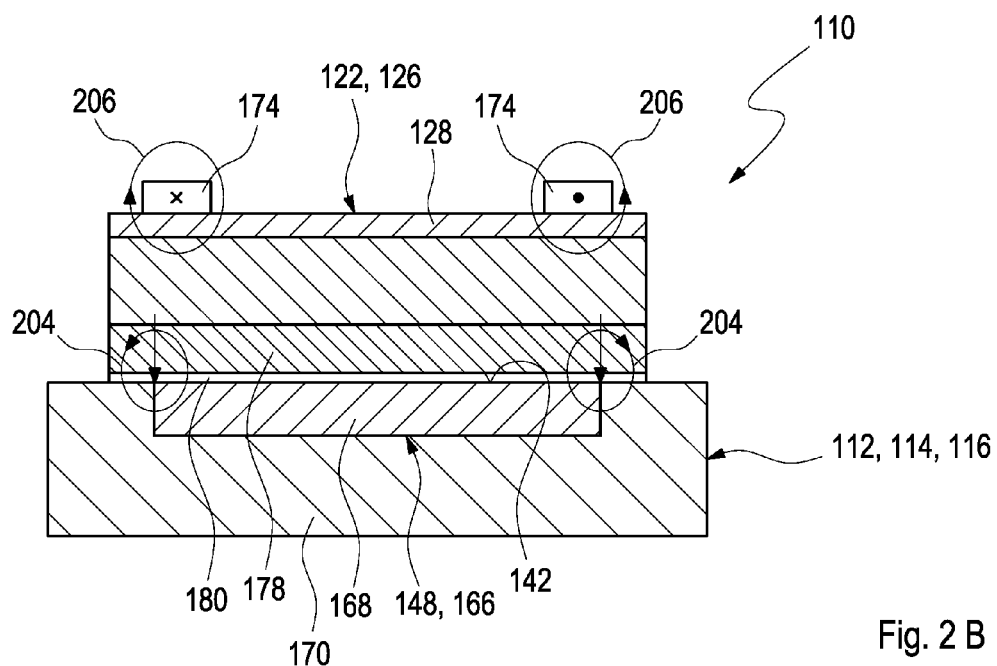

While the exemplary embodiments in FIGS. 1A, 1B and 1C show a generation of an adjustable holding force on the basis of electrostatic principles, FIGS. 2A and 2B illustrate an exemplary embodiment of an insertion device 110, which is based on a magnetic generation of a holding force. The generation is merely illustrated schematically in FIGS. 2A and 2B, with FIG. 2A in turn showing a sectional illustration through the insertion device 110 parallel to a puncture path x (analogously to the illustration in FIG. 1A) and FIG. 2B showing a sectional illustration perpendicular to the image plane in FIG. 2A.

The insertion device 110 in turn comprises an insertion aid 112, which in turn may have a base body 114 in the form of an insertion needle 116. In this respect, reference can largely be made to the above description of FIGS. 1A and 1B. Although an insertion tip 118 has not been shown in this exemplary embodiment, it can nevertheless be present.

The insertion device 110 furthermore in turn comprises a subcutaneous device 122, which can for example in turn be embodied as a subcutaneous sensor 126 and which should for example be implanted into body tissue 124. By way of example, reference can be made to the above description of FIGS. 1A and 1B for the possible embodiment of the subcutaneous sensor 126.

In order to generate an adjustable holding force between the subcutaneous device 122 and the insertion aid 112, the insertion aid 112 in this exemplary embodiment in turn has a first holding element 148, and the subcutaneous device 122 accordingly has a second holding element 152. As illustrated above, the holding elements 148, 152 should generate a holding force $F_H$, which in this case is, wholly or partly, a magnetic holding force $F_B$. The holding elements 148, 152 are accordingly embodied as magnetic holding elements. This can be brought about in various ways: by using permanent magnets and/or by using electromagnets, which can also be combined in an arbitrary fashion. In FIGS. 2A and 2B, this is embodied in a fashion in which the first holding element 148 comprises a permanent magnet 166 with a magnetic pole 168 and a magnetic antipole 170. By way of example, the insertion aid 112 can be produced entirely from a magnetizable or magnetic material, which has been magnetized accordingly. Alternatively, or in addition thereto, the first holding element 148 can also comprise a permanent magnet embedded in a mount material of the insertion aid 112 or a plurality of such permanent magnets and/or at least one magnetically conductive armature lamination.

In the illustrated exemplary embodiment, the second holding element 152 comprises an electromagnetic holding element 172, which comprises a simple printed conductor loop 174 in this exemplary embodiment. It goes without saying that more complex arrangements are also possible. This printed conductor loop 174 is merely illustrated symbolically in FIG. 2A and, as can be identified in FIG. 2B, can for example be applied onto and/or into a mount 128 of the subcutaneous device 122. By way of example, the mount 128 can comprise insulating material, e.g. a plastic, a paper, a ceramic or else a laminate. In principle the use of conductive materials is also possible. In the sectional illustration in FIG. 2B, a possible current direction through the printed conductor loop 174 has been illustrated, wherein the current flows into the plane of the drawing in the left section of the printed conductor loop and flows out of the plane of the drawing in the right printed conductor section. However, a different embodiment is also possible. Current can be applied to the printed conductor loop by a control 144, wherein the control 144 can for example in turn comprise a voltage source and/or a current source 176, and optionally one or more further components, e.g. resistors, capacitors, diodes or else active electronic components. Various embodiments are possible. A person skilled in the art is aware of the principles of the embodiment of a control 144 for controlling an electromagnetic holding element 172.

The control 144 can be designed to set or influence the current through the printed conductor loop 174 in a targeted fashion. In the exemplary embodiment of the control 144 shown in FIG. 2A, this is brought about by pure digital switching on and off. In the process, provision can in turn be made for a switch-over device 158 in order to switch between a switching state $S_1$, in which current is applied to the printed conductor loop 174, and a switching state $S_2$, in which the switch-over device 158 is opened and no current flows. In principle, another embodiment is also possible. Thus, in general terms, the control 144 can for example influence the magnitude of the current strength and/or the direction of the current through the printed conductor loop 174, and so, interacting with the first holding element 148, an attracting or repelling force, or a force of 0, can be generated between the two holding elements 148 and 152. This can for example be explained vividly by virtue of the fact that the permanent magnet 166 generates magnetic field lines, which are denoted symbolically by reference sign 204 in FIG. 2B. These lines are shortened by the substrate armature lamination 178, as a result of which a holding force is generated. The current through the printed conductor loop 174 can be set such that the magnetic field lines 206 surrounding the printed conductor loop 174 counteract the field of the permanent magnet 166, or are directed in the same direction, and so a resulting magnetic overall force can be set and, for example, a repulsive effect can be achieved. Thus, an attractive holding force can be set during the puncturing or when the insertion device 110 is inserted into the body tissue 124, whereas a force of 0 or even a repulsive force can be set between the subcutaneous device 122 and the insertion aid 112 after the puncturing in order to release the subcutaneous device 122 from the insertion aid 112.

In the illustrated exemplary embodiment in FIGS. 2A and 2B, a substrate armature lamination 178 is arranged in an exemplary fashion below the mount 128 in the layered design of the subcutaneous device 122. By way of example, an air gap 180, which can optionally also be wholly or partly filled by at least one insulator, can be below this substrate armature lamination 178, which can for example be produced from a magnetic material, for example a soft-magnetic material, or can comprise such a material. This makes it possible to influence a magnetic force $F_B$. Here, the air gap 180 is merely shown in the illustration as per FIG. 2A, but it can in principle also be inserted into the illustration as per FIG. 2B.

When no current passes through the printed conductor loop 174, a magnetic force from the permanent magnet 166 of the first holding element 148 for example acts on the substrate armature lamination 178 of the second holding element 152. By way of example, the current direction through the printed conductor loop 174 can be selected such that this magnetic holding force is attenuated by the magnetic field generated by the printed conductor loop 174 by the latter magnetic field counteracting the magnetic field from the permanent magnet 166. As a result, the holding force is compensated for, lifted or even overcompensated for. This makes it possible to influence the magnetic holding force by setting the current strength through the printed conductor loop 174 by means of the control 144.

Reference is made to the fact that the illustrated embodiment is merely one of many options of how magnetic holding elements can be used. Thus, the first holding element 148 and/or the second holding element 152 can in general comprise one or more of the following magnetic holding elements: an electromagnetic holding element, for example a printed conductor loop; a permanent magnet; an armature lamination made of a magnetic material, for example a soft-magnetic metal. The first and the second holding element can then for example each generate magnetic fields themselves and/or merely one of these holding elements 148, 152 can generate a magnetic field, which can attract or repel the respective other holding element 148, 152. Various combination options are feasible.

In the illustrated exemplary embodiment, the insertion needle 116 can for example, as explained above, be wholly or partly embodied as a permanent magnet 166, for example by embodying the magnetic pole 168 as a north pole and the magnetic antipole 170 as a south pole or vice versa. The subcutaneous sensor 126 or the subcutaneous device 122 can at least in part be produced from a conductive material. In principle, the use of stainless steel would also be possible for example, but this is less suitable because stainless steel is only weakly magnetic. This makes it possible to form the substrate armature lamination 178, which forms the armature in the vicinity of the magnetic poles 168, 170. As a result, the magnetic field lines are shortened and thereby bring about the holding force during the puncturing. If the subcutaneous sensor 126 or the subcutaneous device 122 is in situ, a current pulse, for example, is applied to the printed conductor loop 174, which runs back and forth on the subcutaneous sensor 126. This current pulse can now bring about a force that counteracts the static magnetic field in the needle and reduces or even lifts the holding force. The insertion needle 116 can then be withdrawn from the tissue, while the subcutaneous sensor 126 remains in the body tissue 124. By way of example, the current pulse can in respect of its time profile and/or shape be synchronized to the withdrawal movement of the insertion needle 116, for example by an appropriate electronic circuit that detects and/or causes the withdrawal movement. This can for example implement a temporally optimum interaction between the forces and the utilized energy can be utilized efficiently. This is particularly preferred in the case of battery operation in particular, for example in the case of an insertion device 110 and/or an insertion aid 112, for example a reusable, with battery operation. As a result of the option of an active control, this can thus achieve an optimum temporal interaction of the forces during the release and withdrawal, and so, for example, dynamic release procedures and/or breaking procedures can also be implemented more effectively. This already allows good results, even with very short current pulses, which is advantageous particularly in the case of a reusable, in which the amount of energy available is generally limited.

Once again, analogously to the exemplary embodiment as per FIGS. 1A and 1B, the force ratios can be calculated, at least approximately. Thus, the following force acts between the first holding element 148 and the second holding element 152 if only the permanent magnet 166 is acting:

$$F_{B,P} = \frac{B^2 * A}{2\mu}. \quad (4)$$

Here, B denotes the magnetic induction of the permanent magnet 166, A denotes the area of the air gap 180 and μ denotes the magnetic permeability, which, according to $\mu=\mu_0 * \mu_r$, is composed from the permeability of the vacuum $\mu_0$ and the relative permeability $\mu_r$ of the material in the air gap 180.

This force $F_{B,P}$ of the permanent magnet is counteracted by the magnetic force of the printed conductor loop 174, which is denoted as $F_{B,L}$ in the following text:

$$F_{B,L} = \frac{\mu * l * I^2}{4 * \Pi * h}. \quad (5)$$

Here, l denotes the length of the printed conductor loop 174, I denotes the current through the printed conductor loop 174, μ once again denotes the magnetic permeability and h denotes the distance between the printed conductor loop 174 and the magnetic substance, for example the permanent magnet 166, on which the printed conductor loop 174 acts in a magnetic fashion. The forces $F_{B,P}$ and $F_{B,L}$ according to equations (4) and (5) above, add to form the overall magnetic holding force:

$$F_B = F_H = F_{B,P} + F_{B,L}. \quad (6)$$

Accordingly, by selecting the direction (i.e. the sign) and the magnitude of the current I and by suitably selecting the materials, it is possible to influence, at this time, the respectively acting holding force by the control 144, from an attractive holding force $F_H$ to a repulsive holding force $F_H$ via the holding force $F_H=0$.

Accordingly, the condition can once again hold during the puncturing that the holding force $F_H$ or the static frictional force caused by this holding force must significantly exceed the overall force acting on the subcutaneous device 122 during the insertion so that the subcutaneous device 122 is not bent or detached from the insertion aid 112 during the insertion. The equation (3) presented above is to be applied accordingly, wherein in this case $F_H$ should be replaced by the overall magnetic holding force described in equation (6).

In the above-described exemplary embodiments in FIGS. 1A to 2B, the assumption was made that the subcutaneous device 122 rests at least in part against a support surface 142 of the insertion aid 112, particularly with its implantable part 134. To this end, the support surface 142 can for example have a flattened embodiment, for example as a flattening on a side of the insertion needle 116, which flattening can for example extend over the entire length of the insertion needle 116 or merely over a part of the length. This support surface 142 preferably has a planar design. In terms of its dimensions, the width of the subcutaneous device 122 is preferably matched to the width of the support surface 142, and so the maximum width of the puncture into the body tissue 124 does not exceed, or only insignificantly exceeds, the maximum width of the subcutaneous device 122 or the implantable part 134 of the subcutaneous device 122.

As illustrated in FIGS. 3A to 3C, the insertion aid 112, in particular the base body 114 thereof, can have such a profiled embodiment, particularly in the region of the support surface 142, that the stability of the insertion aid 112 is increased during insertion. By way of example, FIG. 3A illustrates a triangular profile, FIG. 3B illustrates a trapezoidal profile and FIG. 3C illustrates a circular-arc-shaped profile, for example a semicircular profile. By way of example, this can prevent the insertion needle 116 from bending during the insertion.

As illustrated above, the insertion aid 112, more particularly the base body 114 thereof, or the insertion needle 116 can optionally have an insertion tip 118. This is illustrated symbolically in FIG. 4. Here, it is also shown that the maximum width, denoted by D in FIG. 4, of the insertion tip 118 exceeds the maximum width, denoted by d, of the base body 114 in the region of the support surface 142. As a result, the insertion tip 118 covers, at least in part, an end face 182 of the subcutaneous device 122. As a result of this specially formed "bow", the frontal force $F_F$ (see e.g. FIGS. 1A and 2A) acting on the subcutaneous device 122 during the insertion can be reduced. At the same time, the support surface 142 can open into a ramp 184 on its side facing the insertion tip 118, over which ramp the subcutaneous device 122 can glide after the subcutaneous device 122 is detached from the insertion aid 112 in order to remain in the body tissue 124 while the insertion aid 112 is withdrawn from the body tissue 124. The embodiments as per FIGS. 3A to 3C and/or as per FIG. 4 can in principle be combined with any other exemplary embodiments of the present description, for example as per FIGS. 1A and 1B, 2A and 2B, or 5.

As an alternative to the electrostatic holding principle as per FIGS. 1A and 1B and/or the magnetic holding principle as per FIGS. 2A and 2B, or in addition thereto, use can be made of other principles for generating an adjustable holding force $F_H$. A further principle is illustrated in an embodiment in FIG. 5. In this principle, adhesion forces, which are exerted by an adhesion surface 186, are influenced in a targeted fashion and via electrical action.

Figure 5:
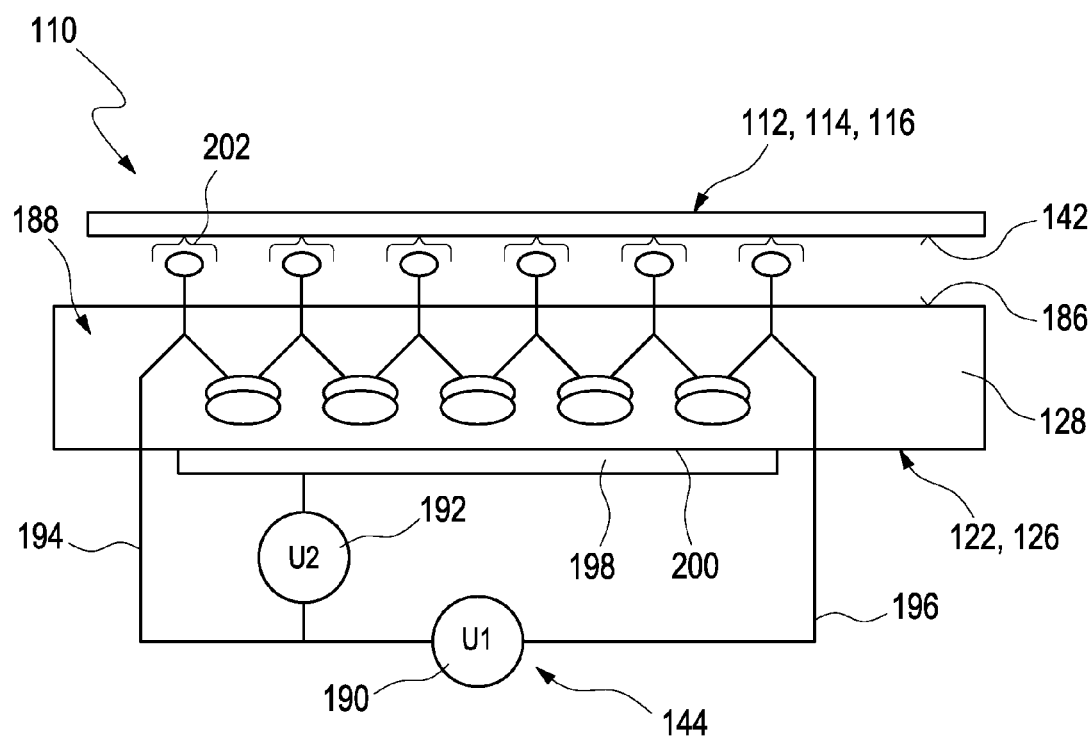
FIG. 5 shows an exemplary embodiment of an insertion device with an adjustable holding force generated by organic electronic structures.

Thus, FIG. 5 for example in turn schematically shows an insertion device 110, wherein reference can largely be made to the description above in respect of the possible embodiments. This insertion device in turn comprises an insertion aid 112, for example with a base body 114 in the form of an insertion needle 116, which is merely indicated schematically in this case. Said insertion aid has a support surface 142, on which a mount 128 (sensor substrate) of the subcutaneous device 122, e.g. of a subcutaneous sensor 126, rests against as a result of adhesion forces. In this exemplary embodiment the adhesion surface 186 is a component of the subcutaneous device 122. However, other embodiments are also possible, i.e. embodiments in which the adhesion surface 186 is a component of the insertion aid 112, for example it may be identical to the support surface 142, and/or embodiments in which both the insertion aid 112 and the subcutaneous device 122 are equipped with interacting adhesion surfaces 186.

In the illustrated exemplary embodiment, the mount 128 has, at least in the vicinity of the adhesion surface 186, an electrically conducting or semiconducting polymer, which is indicated symbolically here and denoted by the reference sign 188. This electrically conducting or semiconducting polymer can for example be wholly or partly embodied as a conjugated polymer, i.e. as a polymer in which double bonds and single bonds alternate. This results in an extended π-electron system, which is responsible for the conducting or semiconducting properties. Polyacetylene can act as a model substance for a polymer conjugated in this fashion. However, alternatively or additionally use can also be made of other conjugated polymers and/or oligomers and/or small molecules that preferably likewise have an extended π-electron system, for example polythiophene, polyparaphenylenevinylene, polyparaphenylene pentacene, tetracene or similar materials, which a person skilled in the art in principle knows from the field of organic electronics.

In the proposed exemplary embodiment, the insertion device 110 in turn has a control 144, by means of which the adhesion properties of the adhesion surface 186 can be influenced in a targeted fashion. To this end, a charge carrier density and/or a conductivity of the adhesion surface 186 can be influenced in a targeted fashion. In the present exemplary embodiment, this is brought about by means of a field effect, analogously to an organic field effect transistor. The control 144 has a first voltage source 190 and a second voltage source 192. While the first voltage source 190 applies a voltage and/or a current to opposing electrodes 194, 196, which are connected by the organic, conducting or semiconducting polymer 188, the second voltage source 192 applies a gate voltage to a gate electrode 198. Insulation 200 can be inserted between the gate electrode 198 and the mount 128. Accordingly, it is possible to influence the potential of the gate electrode 198, which in turn influences a charge carrier density and/or a charge carrier mobility via a field effect and thereby influences conductivity in the region of the adhesion surface 186. The conductivity on the other hand in turn influences the adhesion effect, i.e. the holding force between the insertion aid 112 and the subcutaneous device 122. As explained above, the π-electrons in particular are in most cases material to this conductivity and/or charge carrier density and/or mobility because the π-bridges of the polymer 188 supply mobile charges. The adhesion properties can be modified in a targeted fashion by suitable modification of the polymer 188. Furthermore, at least one adhesion promoter 202, for example an adhesive, can be inserted between the insertion aid 112 and the subcutaneous device 122 in the region of the adhesion surface 186. Said adhesion promoter is symbolically denoted by reference sign 202 in FIG. 5. By way of example, this adhesion promoter 202 can be applied to the support surface 142. By way of example, the adhesion with this adhesion promoter 202 can be influenced in a targeted fashion by changing the charge carrier density and/or the conductivity of the adhesion surface 186.

By influencing the voltages on the voltage sources 190, 192 and/or the currents provided by these voltage sources 190, 192, it is therefore possible to influence the adhesion properties and hence the holding force in a targeted fashion. This also allows targeted influencing of the holding force between the subcutaneous device 122 and the insertion aid 112 by means of the control 144.

A further option, in principle, for increasing adhesion between a subcutaneous device 122 and an insertion aid 112, which option can be used as an alternative to the above-described options, or in addition thereto, consists of influencing the adhesion or the splitting of parts of the insertion device 110 by controlled, external influences. Thus, for example, it is conceivable for stretched films, which are under pretension, to be divided by applying a targeted force, for example by applying force to an outer end of a film of the mount 128, as a result of which this film is ripped or split. By way of example, this can lead to an abrupt change in the adhesion between the insertion aid 112 and the subcutaneous device 122 and/or parts of the subcutaneous device 122.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

| | |
|---|---|
| 110 | Insertion device |
| 112 | Insertion aid |
| 114 | Base body |
| 116 | Insertion needle |
| 118 | Insertion tip |
| 120 | Axis of longitudinal extent |
| 122 | Subcutaneous device |
| 124 | Body tissue |
| 126 | Subcutaneous sensor |
| 128 | Mount |
| 130 | Sensor electrodes |
| 132 | Axis of longitudinal extent |
| 134 | Implantable part |
| 136 | Non-implantable part |
| 138 | Holder |
| 140 | Sensor contacts |
| 142 | Support surface |
| 144 | Control |
| 146 | First electrode |
| 148 | First holding element |
| 150 | Second electrode |
| 152 | Second holding element |
| 154 | Insulator |
| 156 | Magnetoresistor contact |
| 158 | Switch-over device |
| 160 | Voltage source |
| 162 | Short-circuit connection |
| 164 | Puncturing device/retraction device |
| 165 | Additional insulator |
| 166 | Permanent magnet |
| 168 | Magnetic pole |
| 170 | Magnetic antipole |
| 172 | Electromagnetic holding element |
| 174 | Printed conductor loop |
| 176 | Voltage source |
| 178 | Substrate armature lamination |
| 180 | Air gap |
| 182 | End face |
| 184 | Ramp |
| 186 | Adhesion surface |
| 188 | Polymer |
| 190 | First voltage source |
| 192 | Second voltage source |
| 194 | Electrode |
| 196 | Electrode |
| 198 | Gate electrode |
| 200 | Insulation |
| 202 | Adhesion promoter |
| 204 | Magnetic field lines (permanent magnet) |
| 206 | Magnetic field lines (printed conductor loop) |

What is claimed is:

1. An insertion device for inserting a subcutaneous device for detecting an analyte into body tissue, comprising:

an insertion aid having a base body shaped like a needle for insertion into the body tissue; and a subcutaneous device;

wherein the insertion device is configured to generate an adjustable holding force between the base body and the subcutaneous device, the holding force being configured to hold the subcutaneous device against the base body during insertion into the body tissue, and the holding force being adjustable after the insertion such that the subcutaneous device is detachable from the base body; and further wherein the holding force is applied substantially transverse to the direction of movement of the sensor during the insertion.

2. The insertion device of claim 1, wherein the holding force is configured to prevent spatial displacement between the subcutaneous device and the base body in an insertion direction during the insertion.

3. The insertion device of claim 1, wherein the holding force comprises a non-mechanical holding force.

4. The insertion device of claim 1, wherein the insertion device is designed to set the holding force after the insertion to repel the subcutaneous device from the base body.

5. The insertion device of claim 1, wherein the holding force comprises an electrostatic holding force.

6. The insertion device of claim 5 wherein the base body has a first electrode and the subcutaneous device has a second electrode and the insertion device is configured to apply different electric potentials to the first electrode and the second electrode.

7. The insertion device of claim 6, further comprising at least one insulator between the first electrode and the second electrode.

8. The insertion device of claim 1, wherein the holding force comprises a magnetic holding force.

9. The insertion device of claim 8, wherein the insertion aid and/or the subcutaneous device comprises at least one electromagnetic holding element for generating a magnetic field.

10. The insertion device of claim 9, wherein the electromagnetic holding element comprises at least one printed conductor loop.

11. The insertion device of claim 9, further comprising at least one current source configured to generate an adjustable current.

12. The insertion device of claim 1, wherein the insertion device is configured to influence an electric charge carrier density and/or an electric conductivity in the region of at least one adhesion surface of the insertion aid and/or subcutaneous device.

13. The insertion device of claim 12, wherein the influence is generated by a field effect.

14. The insertion device of claim 12, wherein the adhesion surface has at least one conductive or semiconducting organic material.

15. The insertion device of claim 14, wherein the at least one conductive or semiconducting organic material comprises a conjugated polymer.

16. The insertion device of claim 1, wherein the insertion aid comprises a support surface on which the subcutaneous device rests during the insertion.

17. The insertion device of claim 16, wherein the support surface is substantially planar.

18. The insertion device of claim 1, wherein the base body comprises an insertion needle.

19. A method of inserting a subcutaneous sensor into body tissue, comprising:

providing an insertion aid having a base body shaped like a needle;

providing a subcutaneous sensor;

generating an electrostatic or magnetic holding force to hold the base body against the subcutaneous sensor;

inserting the subcutaneous sensor into the body tissue with the insertion aid while the holding force holds the subcutaneous sensor against the base body, wherein the holding force is applied substantially transverse to the direction of movement of the sensor during the insertion;

adjusting the holding force after the insertion; and detaching the subcutaneous sensor from the base body.

20. The method of claim 19, wherein the holding of the subcutaneous sensor against the base body comprises preventing spatial displacement between the subcutaneous sensor and the base body in an insertion direction during the insertion.

21. The method of claim 19, wherein the holding force is generated between electrodes disposed on the subcutaneous sensor and insertion aid.

22. The method of claim 19, wherein the adjusting of the holding force after the insertion comprises repelling the subcutaneous sensor from the base body.

23. The method of claim 19, wherein the base body has a first electrode and the subcutaneous sensor has a second electrode and the generating of the holding force comprises applying different electric potentials to the first electrode and the second electrode.

24. The method of claim 23, further comprising providing at least one insulator between the first electrode and the second electrode.

25. The method of claim 19, wherein the holding force comprises a magnetic holding force.

26. The method of claim 25, wherein the holding force is generated with a printed conductor loop.

27. The method of claim 26, further comprising providing an adjustable current to the conductor loop.

28. The method of claim 19, wherein the step of generating the holding force comprises influencing an electric charge carrier density and/or an electric conductivity in the region of at least one adhesion surface of the insertion aid and/or subcutaneous sensor.

29. The method of claim 28, further comprising generating the influence by a field effect.

30. The method of claim 28, wherein the adhesion surface comprises a conjugated polymer.

31. The method of claim 19, further comprising removing the base body from the subcutaneous sensor while retaining at least a portion of the subcutaneous sensor in the body tissue.

32. The method of claim 31, further comprising measuring with the subcutaneous sensor the presence or concentration of at least one analyte in body fluid in the body tissue.

* * * * *